United States Patent [19]
Lu et al.

[11] Patent Number: 6,032,066
[45] Date of Patent: Feb. 29, 2000

[54] METHOD AND APPARATUS FOR VIRTUAL RADIOTHERAPY BEAM PROJECTION LOCALIZATION IN REAL SPACE

[75] Inventors: Hsiao-Ming Lu, Newton; Lee M. Chin, Wellesley, both of Mass.

[73] Assignee: JCRT Radiation Oncology Support Services, Boston, Mass.

[21] Appl. No.: 09/007,782

[22] Filed: Jan. 15, 1998

Related U.S. Application Data

[60] Provisional application No. 60/039,317, Feb. 7, 1997.

[51] Int. Cl.[7] ....................................................... A61B 6/00
[52] U.S. Cl. .............................. 600/407; 128/920; 378/65
[58] Field of Search .................................... 600/300, 407, 600/409, 415, 427, 429, 439; 128/920; 378/65, 205–208

[56] References Cited

U.S. PATENT DOCUMENTS

| | | | |
|---|---|---|---|
| 3,838,212 | 9/1974 | Whetstone et al. | 179/18 |
| 4,891,474 | 1/1990 | Kelly | 178/18 |
| 5,043,950 | 8/1991 | Schorum et al. | 367/98 |
| 5,050,134 | 9/1991 | Butler | 367/118 |
| 5,054,005 | 10/1991 | Schorum | 367/127 |
| 5,107,839 | 4/1992 | Houdeh et al. | 600/415 X |
| 5,391,139 | 2/1995 | Edmundson | 600/7 |
| 5,411,026 | 5/1995 | Carol | 600/439 |
| 5,447,154 | 9/1995 | Cinquin et al. | 600/429 |
| 5,483,961 | 1/1996 | Kelly et al. | 600/429 |
| 5,517,990 | 5/1996 | Kalfos et al. | 600/429 X |
| 5,588,430 | 12/1996 | Bova et al. | 606/130 X |
| 5,810,007 | 9/1998 | Holupka et al. | 600/439 |

OTHER PUBLICATIONS

Kato, Amami et al., "A Frameless, Armless Navigational System for Computer–Assisted Neurosurgery," *J. Neurosurg.* 74:845–849 (May 1991).

Tan, Kim K. et al., "A Frameless Stereotactic Approach to Neurosurgical Planning Based on Retrospective Patient–Image Registration," *J. Neurosurg.* 79:296–303 (Aug. 1993).

Reinhardt, H.F. and Zweifel, H.–J, "Interactive Sonar–Operated Device for Stereotactic and Open Surgery," *Proceedings of the Xth Meeting of the World Society for Stereotactic and Functional Neurosurgery*, Maebashi, Japan (Oct. 1989), vol. 54, 55, pp. 393–397.

Mösges, Ralph and Schlöndorff, "A New Imaging Method for Intraoperative Therapy Control in Skull–Base Surgery," *Neurosurg. Rev* 11:245–247 (1988).

Primary Examiner—Francis J. Jaworski
Attorney, Agent, or Firm—Hamilton, Brook, Smith & Reynolds, P.C.

[57] ABSTRACT

A computer system to project and localize radiation treatment portals, i.e., field center, field borders, on patient skin without using a light field is disclosed. The system includes a multimedia software program that interacts with a three-dimensional digitizer which acquires the coordinates of any point in space that is accessible by the digitizer probe. The system constructs and employs coordinate system transformations from digitizer coordinates to room coordinates to radiation beam coordinates. For any point digitized, the invention system calculates the position of this point relative to the radiation field, and displays or signals to the user whether the digitized point is in the radiation field, outside of the field or on the field border. This is accomplished through a screen display of the radiation beam's eye view, an audio signal and/or LED light indicators mounted on the digitizer probe.

20 Claims, 4 Drawing Sheets

METHOD AND APPARATUS FOR VIRTUAL RADIOTHERAPY BEAM PROJECTION LOCALIZATION IN REAL SPACE

RELATED APPLICATIONS

This application claims the benefit of U.S. Provisional Application No. 60/039,317 filed Feb. 7, 1997, the contents of which is incorporated herein by reference in its entirety.

BACKGROUND

"Radiotherapy" is the use of radiation in treating cancer or cancer related disorders/illnesses. Each therapy program has a radiation dosage defined by type and amount of radiation for each treatment session, frequency of treatment session and total of number of sessions. In addition, the radiation may be delivered internally or by an external beam. Each of these factors and hence the radiation treatment program may be different for different patients/cases. In addition, there are a variety of devices or machines for planning and delivering the radiation at the prescribed doses, for instance, a CT scanner, a conventional simulator, a Cobalt-60 teletherapy machine, a linear accelerator, an after-loader for radioactive sources, and the like.

In external beam radiation therapy treatment, highly directional fluxes of high energy photon and/or electronparticles are delivered by medical linear accelerators or Cobalt-60 machines into the patient's body, through a specifically collimated cross section, often referred to as the "field" with reference to the patient. Angle of entry and shape of the radiation beam from such a machine is as carefully planned on a patient by patient basis as the radiation dosage itself. To illustrate this point, a typical scenario in providing radiotherapy to a cancer patient is as follows.

After the decision for radiotherapy has been made, a subject patient attends a planning session with the radiation oncologist and a medical physicist. At the planning session, all the diagnostic data (CT scans, radiographs, MRI scans) are assembled for the purpose of defining the target to be treated and the surrounding critical normal tissues to be spared. The patient is then placed under a simulator which mimics in all aspects the radiotherapy machine for the treatment, except that the beam from the simulator is a diagnostic X-ray beam. Since the radiation dosage from this diagnostic beam is very low compared to the treatment beams, many treatment scenarios can be simulated to assess the best combination of beams to hit the target and spare the normal tissues. The internal structures of the patient for the corresponding field are assessed by taking a radiograph. External coverage is assessed by looking at an outline of the radiation beam on the patient's skin which is typically visualized by using a radiologically divergent light source collimated identically through the aperture of the real radiation beam. This collimated light projection is called the "light field".

Conventional simulators and treatment machines are equipped to provide the light field. The projection of the light field on the patient's skin simulates the geometry of the real treatment (radiation) beam. The simulation process allows the radiation oncologist to evaluate the patient's external anatomy relative to the radiation beam and to mark particular entry points, e.g., the field center, field corners, to be used as reference points later in the treatment sessions. That is, during the projection of the light field on the patient, the radiologist uses a pen (or ink) to mark indications of the field center and corners on the patient's skin. In order to reproduce the simulated treatment, the light field of the treatment machine is aligned to these markings/indications at the beginning of each treatment/dosage.

One disadvantage of the above conventional simulation process is the existence of large uncertainties in the correlation of diagnostic data (e.g., CT, MRI) taken elsewhere and applied to the treatment position which is usually different from the position that the patient was set up for the diagnostic data. Yet it is extremely valuable to obtain 3-dimensional patient information for planning purposes. An alternative process is to use a CT-scanner to provide 3-dimensional patient information but scan the patient in the treatment position. This is becoming the state-of-the-art "simulation" process. However, the disadvantage of the new approach using the CT-simulator is that it is not usually equipped to produce the light field for the purpose described above. In those machines which produce a light field, patient setup for multi-beam treatment is time consuming and cumbersome, since the alignment of the light field with the markings have to be confirmed for all the beams before the treatment can start and yet this can only be done one beam at a time involving the motions of heavy machinery. Moreover, since the light field can only show the entrance point on patient skin surface, but not the exit points, the matching of opposite beams, as often required by the treatment, can be difficult.

Thus there is a need for an efficient and accurate system to project and localize treatment beams when CT-scanners are used for simulation.

SUMMARY OF THE INVENTION

The present invention overcomes the problems of the prior art. In particular, applicants have developed a system to perform the beam projections and localizations for both simulation and/or treatment without actually using a light field or radiation exposure.

Applicants' system is a multimedia software that interacts with a three-dimensional digitizer which acquires the coordinates of any point in space that is accessible by the digitizer probe. It does not generate a real light field projection on the patient's skin, but instead, it establishes a virtual beam on the patient. This virtual beam projection is not visible to the human eye, but is visible to the 3D digitizer probe. For any point digitized, the computer calculates its position relative to the radiation field, and indicates to the user whether this point is in the radiation field, outside of the field, or on the field border. In the preferred embodiment, the indication is made through a beam's eye view display, audio signal, and LED light panel mounted on the digitizer probe handle.

Accordingly, the preferred embodiment provides apparatus for aligning a subject area with respect to a radiation beam where the radiation beam has a respective coordinate system. The invention apparatus includes a digitizer probe, a 3D digitizer, a computer processor assembly and a display assembly.

The digitizer probe is formed of a handle and an elongate body having one end coupled to the handle and a distal end opposite the one end, across the length of the elongate body. The distal end is used for pointing to a point on the subject area. Specifically, the probe has a longitudinal axis along the length of the elongate body and through the distal end of the probe. The intersection of the longitudinal axis and the subject area defines the subject point. The handle has a transmitter for generating a working signal, such as a sound wave signal.

The 3-D digitizer has (i) a receiver spaced apart from the digitizer probe and the subject area for receiving the working signal from the transmitter, and (ii) digitizing means coupled to the receiver and responsive to the received working signals. The receiver preferably includes a plurality of detectors (e.g., microphones) for receiving the sound wave signals (e.g., sound waves) at different distances and hence different times. The digitizing means records the different receipt times or otherwise generates the time of flight for the signals. The digitizing means employs a digital processor to calculate and digitize coordinates of the point on the subject area, pointed to by the probe distal end, in a coordinate system of the 3-D digitizer. As such, the 3-D digitizer generates coordinates of the subject point. In particular, the digital processor employed by the digitizing means utilizes a triangulation or other suitable calculation for determining distance based on the different receipt times. From the determined distance, the digitizing means determines digitizer coordinates of the subject point.

The computer processor assembly is coupled to the 3-D digitizer for receiving the digitizer coordinates of the subject point. In turn, the computer processor assembly transforms the digitizer coordinates into coordinates of the radiation beam coordinate system.

The display assembly is coupled to the computer processor assembly and displays the indication of location of the point pointed to by the distal end of the probe, with respect to intersection of the radiation beam with the subject area. To that end, the display and hence invention apparatus enables the subject area to be correlated or mapped to the radiation beam.

In accordance with one aspect of the present invention, one may either digitize points of clinical or anatomical interest, e.g. breast tissue extents, excisional scar position, to see if they are included in the field with sufficient margin, or one can cruise the digitizer probe along the patient's skin to locate the radiation field borders and the specific field points for patient marking. The invention apparatus thus provides the same information that is conventionally obtained with the use of a real light field. Moreover, the invention apparatus is particularly useful in radiation treatment planning and patient setup procedures involving the matching of multiple radiation beam fields, since it can show both the entrance and exit point of the radiation beam as intersected with the patient, while a real light field only shows the entrance point.

In accordance with another aspect of the present invention, the computer processor assembly cooperates with a radiation diagnostics computer system.

In accordance with another aspect of the present invention, the display assembly includes a monitor for displaying a screen view indication of the radiation beam coordinate system overlaid with the indication of the location of the subject point. Further, the display assembly includes an LED light assembly coupled to the probe (e.g., probe handle) for indicating location of the subject point relative to boundaries of the radiation beam as intersected with the subject area. Preferably, the LED light assembly includes a red light for indicating that the subject point lies outside of the radiation beam boundaries, a yellow light for indicating that the subject point lies on the radiation beam boundaries and a green light for indicating that the subject point lies inside the radiation beam boundaries.

BRIEF DESCRIPTION OF THE DRAWINGS

The foregoing and other objects, features and advantages of the invention will be apparent from the following more particular description of preferred embodiments and the drawings in which like reference characters refer to the same parts throughout the different views. The drawings are not necessarily to scale, emphasis instead being placed upon illustrating the principles of the invention.

DETAILED DESCRIPTION OF THE PREFERRED EMBODIMENT

Figure 1:
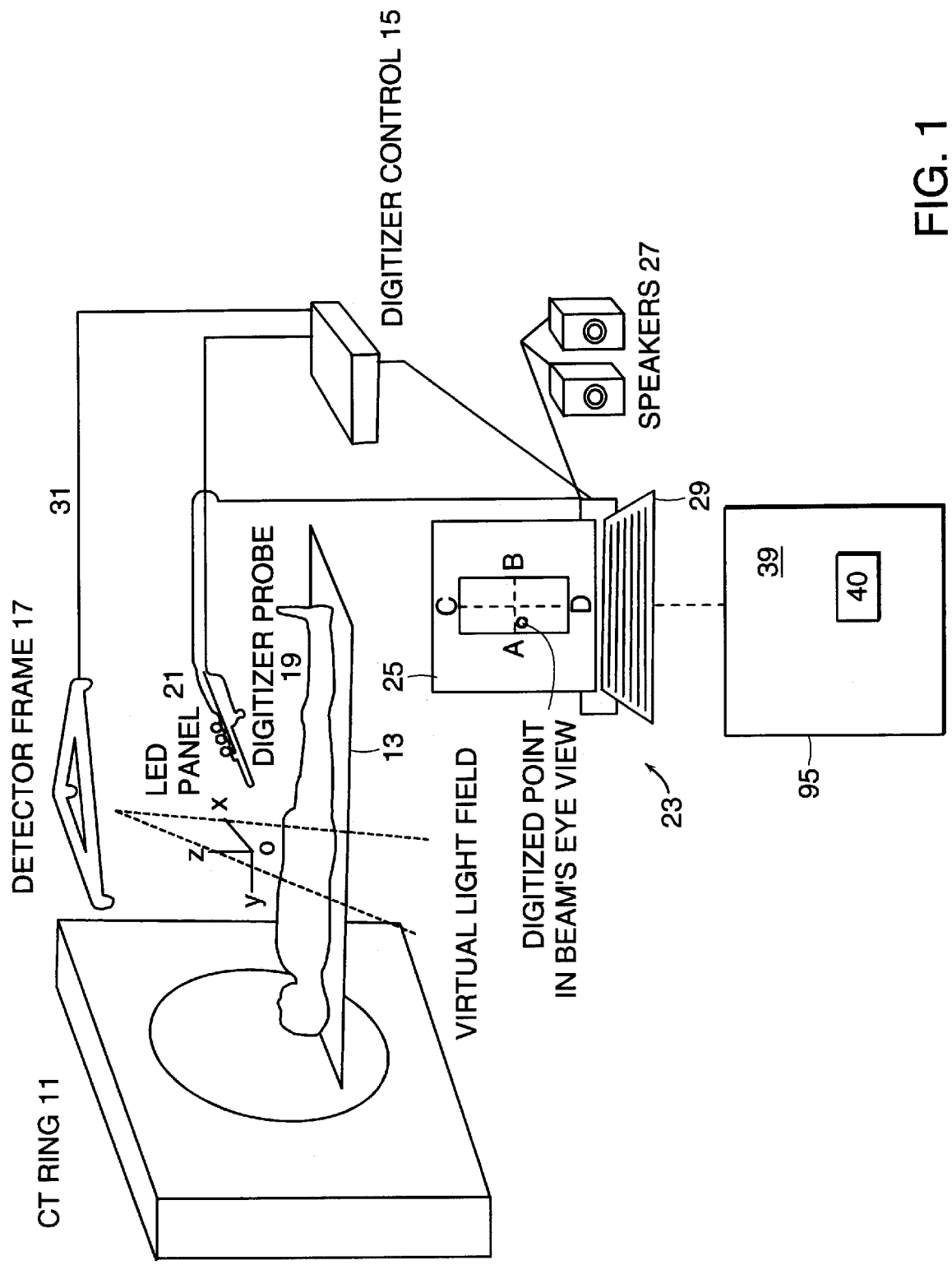
FIG. 1 is a schematic diagram of a preferred computer based apparatus embodying the present invention.

Illustrated in FIG. 1 is a preferred embodiment of the present invention. The invention computer system and apparatus is assembled for operation in the room of a CT scanner or other machine chosen to simulate or deliver the prescribed radiation dosage of a patient. In particular, the invention computer system and apparatus is set up for use alongside the radiation machine 11 and associated patient couch (work surface) 13. Included in the present invention's system is a 3-D digitizer assembly 15, 17, 19 and a computer terminal 23 coupled to the 3-D digitizer assembly. The 3-D digitizer assembly is formed of a digitizer probe 19, a receiver/detector 17 and a digitizing processor member 15, which are supported by the computer terminal 23.

The computer terminal 23 includes a PC or other digital processor 39 having the capabilities of an Intel XX486 or better processing chip. The computer terminal 23 also includes I/O (input/output) peripherals such as a keyboard 29, mouse, display monitor 25 and audio speakers 27. Further, the computer terminal 23 may be coupled to a radiology diagnostics and therapy planning computer system 95 such as General Electric's Advantage Sim. Other such diagnostics and therapy planning computer systems are suitable as long as they provide radiation beam data and imaging data of a patient including cross-sectional views and radiation beam data.

Typically the computer terminal 23 and digitizing processor member 15 of the 3-D digitizer assembly are positioned to one side of the patient couch 13 or working surface of the radiation machine 11, while the receiver/detector 17 is secured to the ceiling over the patient couch 13. The digitizer probe 19 is connected to the digitizing processor member 15 with a cord having a length that allows use around various sides of the patient couch 13. Further, the digitizer probe 19 is coupled to the computer terminal 23 as further discussed below.

In the preferred embodiment, the 3-D digitizer assembly is a GP12XL Sonic Digitizer (by Science Accessories Corp.), but any three-dimensional digitizer with effective detection space equal to or greater than a cube of 1.5×1.5× 1.5 meters and with a position detection accuracy better than two millimeters may be used. The digitizer probe 19 is generally L-shaped having a handle and an elongate body. One end of the elongate body is attached to the handle while a distal end lies opposite the one (handle) end across the length of the elongate body. The elongate body has as a longitudinal axis that extends from the distal end to a subject area of the patient. The intersection of the longitudinal axis and subject area defines a point location to which the probe distal end is pointing. In the preferred embodiment, the tip of the distal end makes physical contact with the subject area and defines the point location to which the probe is pointing.

The probe 19 handle houses a plurality of sound emitters. In the preferred embodiment, two sound emitters are employed. The digitizing processor member 15 drives the sound emitters to generate a sound signal or sound wave. The generated sound waves/signals are received by the ceiling mounted receiver/detector 17. In the preferred embodiment, the receiver/detector 17 houses three microphones spaced apart from each other in a triangular pattern for receiving the sound waves/signals. The microphones or receiver/detector 17 are connected to the digitizing processing member 15 across line 31.

The digitizing processing member 15 records the amount of time that has passed from emission of the sound signal, by each emitter of the probe 19, to receipt of the sound signal, by the microphones. The digitizing processor member 15 passes this recorded amount of time to a digital processor for calculating the distance traveled by the sound waves and hence the distance from each emitter of the digitizer probe 19 to the receiver/detector 17. In particular, the digital processor employed by digitizing member 15 performs a distance calculation by triangulation techniques as is commonly known (see 3D Digitizing Systems, Science Accessories Corporation, 1993). In turn, the digital processor uses the calculated distances of each emitter to define a line (where two point locations of the emitters define a line). The longitudinal axis of the probe elongate body lies along the defined line. As such, the digital processor further uses the calculated distances (or defined line) to provide coordinates of the digitizer probe 19 distal end and hence subject point to which the distal end is pointing. The generated coordinates are in terms of the 3-D digitizer assembly coordinate system.

U.S. Pat. Nos. 3,838,212, 4,891,474, 5,043,950, 5,050,134 and 5,054,005 further explain the details of 3-D digitizer assembly and said teachings are herein incorporated by reference.

In the preferred embodiment, digitizing processor member 15 is coupled via line 33 to the digital processor 39 of the computer terminal 23. As such, digital processor 39 calculates the distance traveled by probe signals and in turn generates the digitizer coordinates of the subject patient. However, other architectures of digitizing processor member 15 may be used where a digital processor is combined with or otherwise functionally tied to digitizing processor member 15, to achieve the foregoing results.

Referring back to FIG. 1, the 3-D digitizer assembly digitizes and generates digitizer coordinates of point locations of points to which the probe 19 distal end is pointed. The digital processor 39 at computer terminal 23 further provides a software program 40 or other processing means for transforming the generated digitizer coordinates of subject points to the radiation beam coordinate system of the room radiation machine 11. Details of the transformation are discussed later. With the results of this transformation, software program 40 supports display through I/O means (e.g., LED's 21 and screen 25) of an indication of the subject point relative to the radiation beam boundaries, i.e., radiation beam intersection with the patient.

Figure 2:
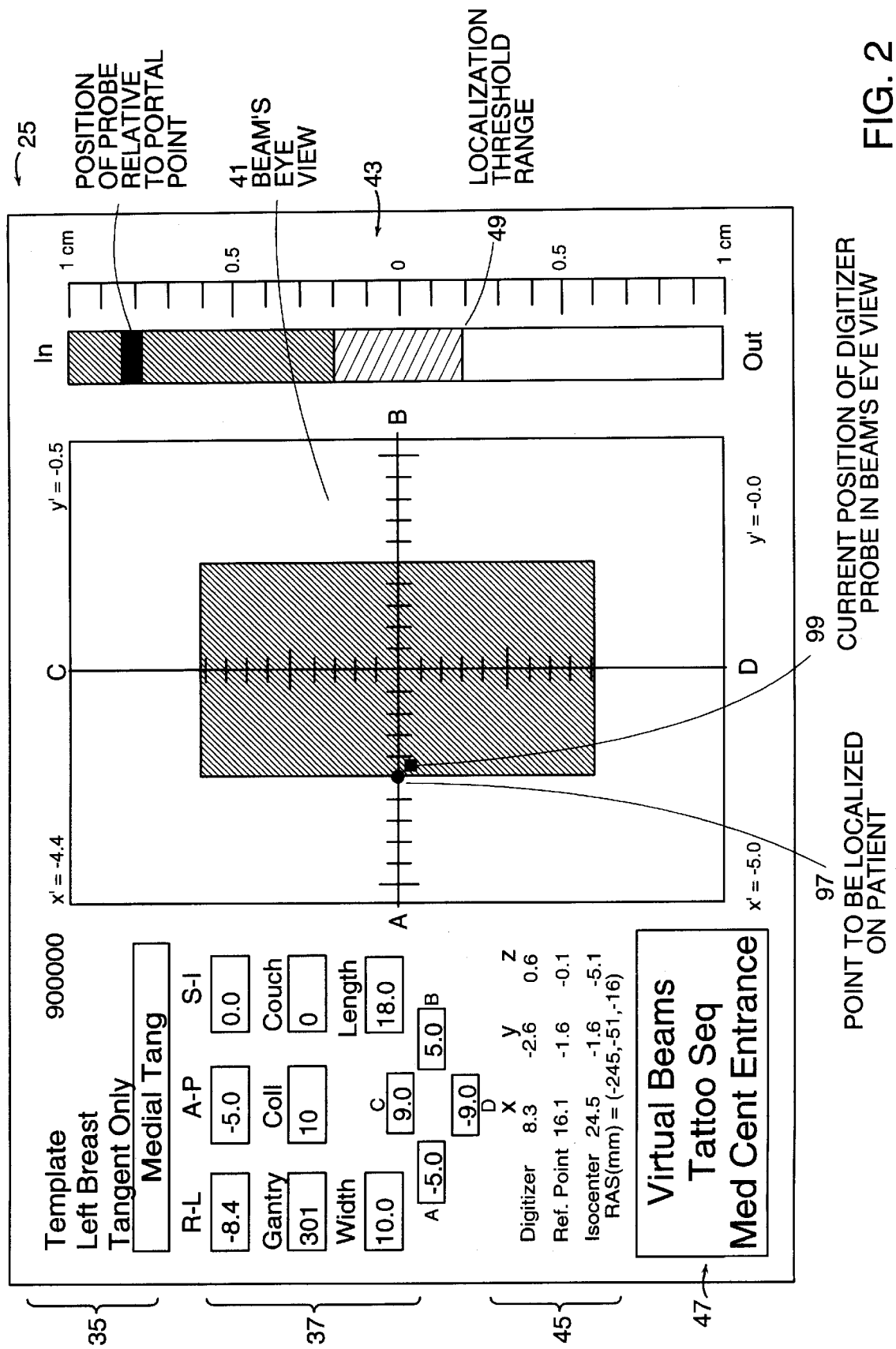
FIG. 2 is an illustration of a screen view generated by a computer in the apparatus of FIG. 1, during patient marking mode.

One such indication is a screen view displayed at the computer terminal monitor 25 as illustrated in FIG. 2. In that screen view, the field borders 41 of the radiation beam as projected on the subject area is shown with the location 99 of the digitized point (the point to which the distal end of the probe 19 is pointed) overlaid on the radiation beam field boundaries or borders 41. In particular, during patient tattooing or marking mode, the screen view in FIG. 2 includes the following.

A scale at the rightmost part of the screen, with a bar graph indicator 43 indicates the distance from the current position of the digitizer probe 19 (distal end) to a predetermined (reference) point to be located. That is, the invention software program 40 calculates the projected distance from the digitized point to the nearest radiation field border and illustrates the calculated distance on the displayed bar graph 43 so that one can conveniently see the relative location of a subject point with reference to the edges of the radiation beam. Preferably, various shading is used in the bar graph 43 to illustrate relative location thresholds of "IN", "OUT" and "localized" 49.

In the central part of the screen view, the radiation beam's eye view is displayed together with four edges defining the radiation beam (darker shaded interior rectangular area in FIG. 2), the location of the predetermined (e.g. tattoo or reference) point 97 to be found, and current position 99 of the digitizer probe 19 distal end. Patient information 35 and the radiation beam parameters 37 are displayed on the left part of the screen view. The radiation beam coordinates of the reference point 97, the isocenter (unique reference point of a treatment unit, usually the rotational center of a vertical gantry which contains the radiation source) for the current beam, and the point location pointed to by the digitizer probe 19 are also displayed at the lower left quadrant area 45. An "action" panel 47 is shown at the lower left corner to indicate the stage of the invention software program 40 and the required action.

In addition, the invention software program 40 provides an indication of the location of the digitized points with respect to radiation beam field border (i.e., the intersection of the radiation beam and the subject patient area) through an LED light panel 21 attached to the digitizer probe 19. That is, the software program 40 in response to calculating and determining the coordinates of the subject point with respect to the radiation beam coordinate system, generates output to the LED light panel 21 as follows.

The computer means (software program) 40 enables a green LED to illuminate on the LED light panel 21 when the determined coordinates of the subject point are determined to be inside the radiation beam field (i.e., boundaries of the radiation beam intersection with the patient subject area). The computer means 40 enables a yellow LED to be illuminated when the calculated coordinates of the subject point fall on the radiation field border, and a red LED to be illuminated on the light panel 21 when the calculated coordinates of the subject point fall outside of the radiation beam field. Further, the computer means/software program 40 generates output signals for illuminating all three LED's (green, yellow and red) on the light panel 21 when the coordinates of the subject point are determined to be on the preselected/target (tattoo or reference) point, and the green and yellow LED's to be illuminated together when the coordinates of the subject point are determined to lie on the x or y axis inside the radiation field.

Other light patterns or LED light panel configurations are suitable. In sum, the LED light panel 21 provides an immediate and locationally convenient means of feedback to the probe operator, in order to align the subject area with the radiation beam during treatment planning. More accurately, the LED light panel 21 enables the operator to "see" where the probe 29 is pointed to relative to the radiation field, without requiring the operator to take his eyes off the patient and look at the computer monitor 25.

Accordingly, the present invention apparatus enables one to digitize any point of concern on the patient and find its corresponding position in the radiation beam's eye view.

In the procedure to locate special field points for patient marking, one first selects the intended point in the beam's eye view and sets the digitizer 15 to the so-called "line mode". In this mode, the digitizer processor 15 continuously captures the positions pointed to by the probe 19 distal end as the operator cruises the probe 19 over the patient. At each digitization, the point location pointed to by the probe 19 is transformed and projected onto the radiation beam's field. Then the projected distance between the working point currently pointed to by probe 19 and the previously selected, intended point is calculated. When the calculated distance is smaller than a specified margin, e.g. 2 mm, the field point is considered to be successfully located. The operator is then informed by screen display 25, audio signal and LED light panel 21 indications, so that he may mark the current position of the working point pointed to by probe 19 as the intended field point.

In the preferred embodiment, the LED light panel 21 indication, screen display 25 and audio signal through speakers 27 (FIG. 1) are presented to the operator, at the same time. The audio signal may be a bell or chime or the like. The LED display 21 may flash the green, yellow and/or red LED's in a synchronous or other manner with respect to the audio signal. Various signal patterns and configurations are within the purview of one skilled in the art. A main purpose of the various output signals is to timely, efficiently and conveniently apprise the operator of the significance of the working point (i.e., the current point location on the patient pointed to by the probe 19 distal end).

In order to transform the generated digitizer coordinates to radiation beam coordinates, the present invention software program 40 first transforms the digitizer coordinates to the room coordinate system. The room coordinate system is established for software program 40 at the time of initialization or calibration of the invention system/apparatus as follows.

Figure 3:
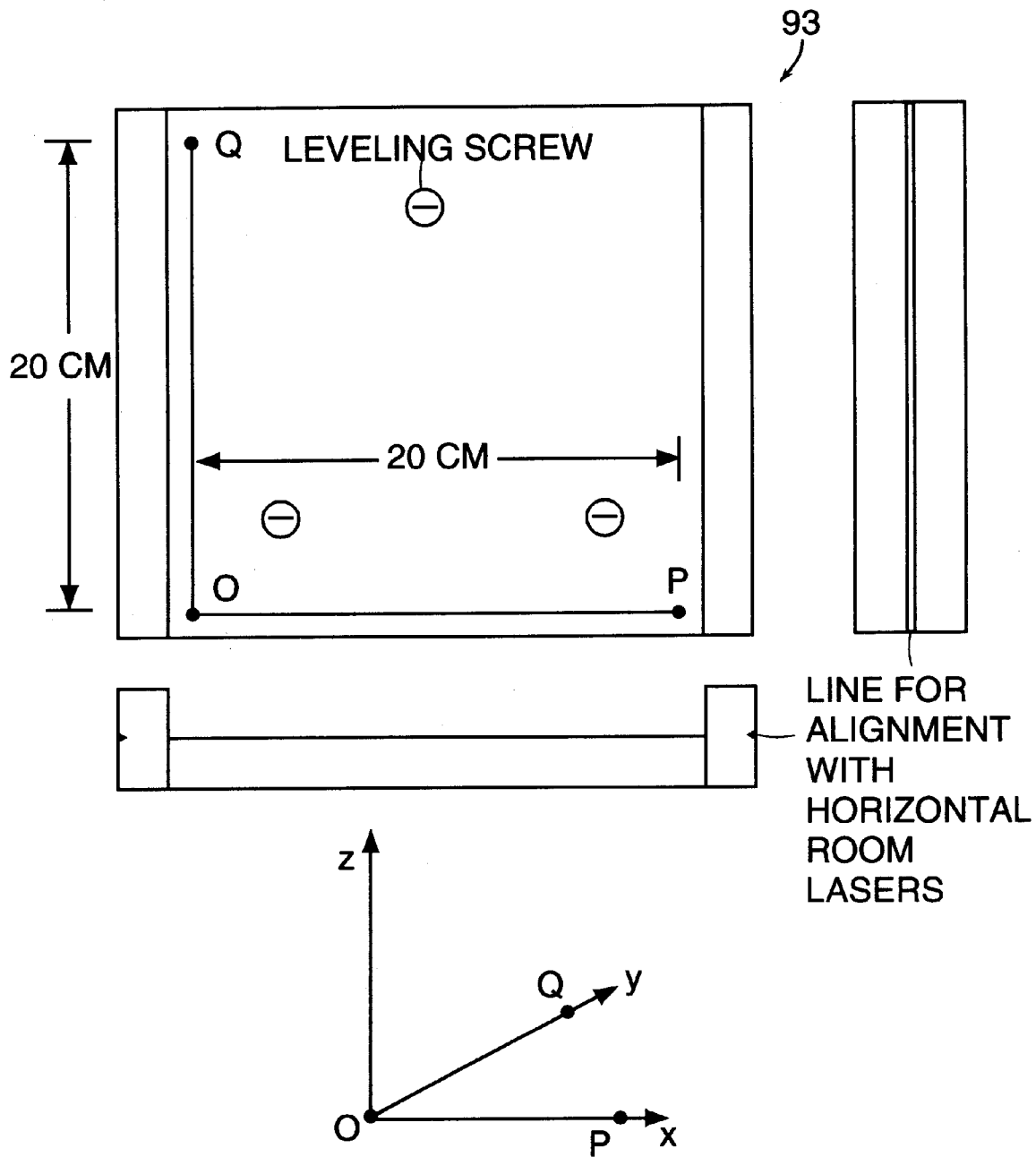
FIG. 3 is a schematic illustration of a calibration device and procedure used for calibrating the apparatus of FIG. 1.

A calibration procedure and device as illustrated in FIG. 3 is employed to obtain working transformation matrices for enabling transformation from the digitizer coordinate system to room coordinate system. The calibration device 93 includes a generally rectangular plate measuring about 20 centimeters on a side. The plate is aligned with the room coordinate system. The plate is placed in the room (on the wall of FIG. 1 for example) such that the indicated point O is at the origin of the room coordinate system; point P is on the positive x axis; and point Q is on the positive y axis. Very often the room coordinate system is specified by using lasers mounted on the ceiling and walls. These laser lights provide projections of the axes of the room coordinate system. The dark lines inscribed on the device 93 in FIG. 3 are to be aligned with the room lasers.

By digitizing (i.e., pointing the distal end of the digitizer probe 19 and operating the probe 19 on) the three points O, P, Q, one obtains the digitizer coordinates of the room coordinate system origin $r_o$, $r_p$, $r_q$. Since the relative positions of the three points are known, the invention system software program 40 calculates the unit vectors i, j, k of the x, y, z axes, respectively, of the room coordinate system as $i=(r_p-r_o)/|r_p-r_o|$, $j=(r_q-r_o)/|r_q-r_o|$, $k=i\times j$ For any point digitized, the software program 40 then transforms the digitizer coordinates r=(x, y, z) in the 3-D digitizer assembly coordinate system to r'=(x', y', z') in the room coordinate system according to $x'=(r-r_o)\cdot i$, $y'=(r-r_o)\cdot j$, $z'=(r-r_o)\cdot k$ Next the room coordinate system point r' is transformed to the radiation beam coordinate system, or the collimator coordinate system, which is defined such that its origin is at the isocenter and its z-axis points to the position of the radiation source. In treatment machines or in the conventional simulator, the isocenter is just the origin of the room coordinate system. Therefore, the transformation constitutes only rotations corresponding to the gantry, couch and collimator angles of the radiation beam. But in CT-Simulation, the isocenter is defined in the CT data of the cooperating radiology diagnostics computer system and is not related to the room coordinates. Then an additional shift is required to shift r' to a virtual room coordinate system that is realized at the treatment machine. This virtual isocenter position is obtained by using a reference point selected on the patient. During the CT-Scan a radio-opaque marker is placed at the reference point and its coordinates are obtained from the CT data (i.e., the radiology diagnostics computer system). After the radiation beams have been planned on the CT data, the shift $V'_s$ from the patient reference point to the virtual isocenter may then be deduced. The reference point $V'_r$ is then digitized and the invention software 40 calculates the virtual isocenter position in the room coordinate system as $V'_{iso}=V'_s+V'_r$.

Then for any working points digitized during use of the invention apparatus, the software program 40 shifts the digitizer coordinates r' by $V'_{iso}$ and then applies the rotations to obtain the corresponding coordinates r" in the collimator (radiation beam) coordinate system as follows.

$r''=R_c R_g R_t(r'-V'_{iso})$ where $R_c$ $R_g$ $R_t$ are rotation matrices defined as $$R_c = \begin{bmatrix} \cos(\theta_c) & \sin(\theta_c) & 0 \\ -\sin(\theta_c) & \cos(\theta_c) & 0 \\ 0 & 0 & 1 \end{bmatrix}$$

$$R_g = \begin{bmatrix} \cos(\theta_g) & 0 & \sin(\theta_g) \\ 0 & 1 & 0 \\ \sin(\theta_g) & 0 & \cos(\theta_g) \end{bmatrix}$$

$$R_t = \begin{bmatrix} \cos(\theta_t) & \sin(\theta_t) & 0 \\ -\sin(\theta_t) & \cos(\theta_t) & 0 \\ 0 & 0 & 1 \end{bmatrix}$$

with $\theta_g$, $\theta_t$, and $\theta_c$ being the gantry, table and collimator angles, respectively.

The next step is to radiologically project r" onto the isocenter plane, which is the xy-plane of the radiation beam coordinate system. The coordinates of the projected point (X, Y) in the isocenter plane are calculated as $X=x''SAD/(SAD-z'')$ $Y=y''SAD/(SAD-z'')$ where SAD is the distance from the position of the radiation source to the origin of the radiation beam coordinate system.

X and Y gives the position of the digitized point in the radiation beam's eye view (i.e., radiation beam coordinate system).

Thus working points on the subject area of the patient are pointed to by the distal end of digitizer probe 19 and digitized by the 3-D digitizer assembly 17, 15. The resulting digitizer coordinates of the working points are then transformed by the invention software program 40 to coordinates in the radiation beam coordinate system. In turn the software program 40 generates and displays the indication of the determined point location of the working point with respect to the intersection of the radiation beam and the subject area of the patient, as illustrated in FIG. 2 and discussed above.

In addition to the foregoing operation and use of the invention computer system and apparatus for patient marking (tattooing) and treatment planning, the software program 40 supports use of the digitizer probe 19 as an input device to computer terminal 23. In particular, a subroutine of program 40 enables the operator to make a menu choice using the digitizer probe 19 instead of the mouse or keyboard 29. In turn, the operator does not have to walk to the computer console 23 during patient marking (tattooing) or a treatment planning. The use of probe 19 as an input device to computer 23 is as follows.

For every point digitized, the invention program 40 computes the distance from the origin of the room coordinate system to the digitized point. If the distance is greater than a threshold value, e.g., 70 cm, the digitization will not be treated as patient data input, but as a signal for a menu selection. In turn, program 40 enters a remote menu mode which results in the display of a screen view with a number of buttons (or activation areas) corresponding to the available and relevant menu selections at the present stage of the software 40. The program 40 illuminates or brightens the buttons/activation areas sequentially, one at a time. The program 40 supports simultaneous generation of a voiced announcement (played through speakers 27) with each button illumination, so that the operator does not have to look at the computer screen (monitor) 25 for the displayed highlighted menu selections. To make a specific selection, the user digitizes at any point (using probe 19) when the desired button is brightened. The software program 40 understands that the digitization is the signal to choose the menu selection corresponding to the currently illuminated button and act (i.e., process the menu selection) accordingly.

Figure 4:
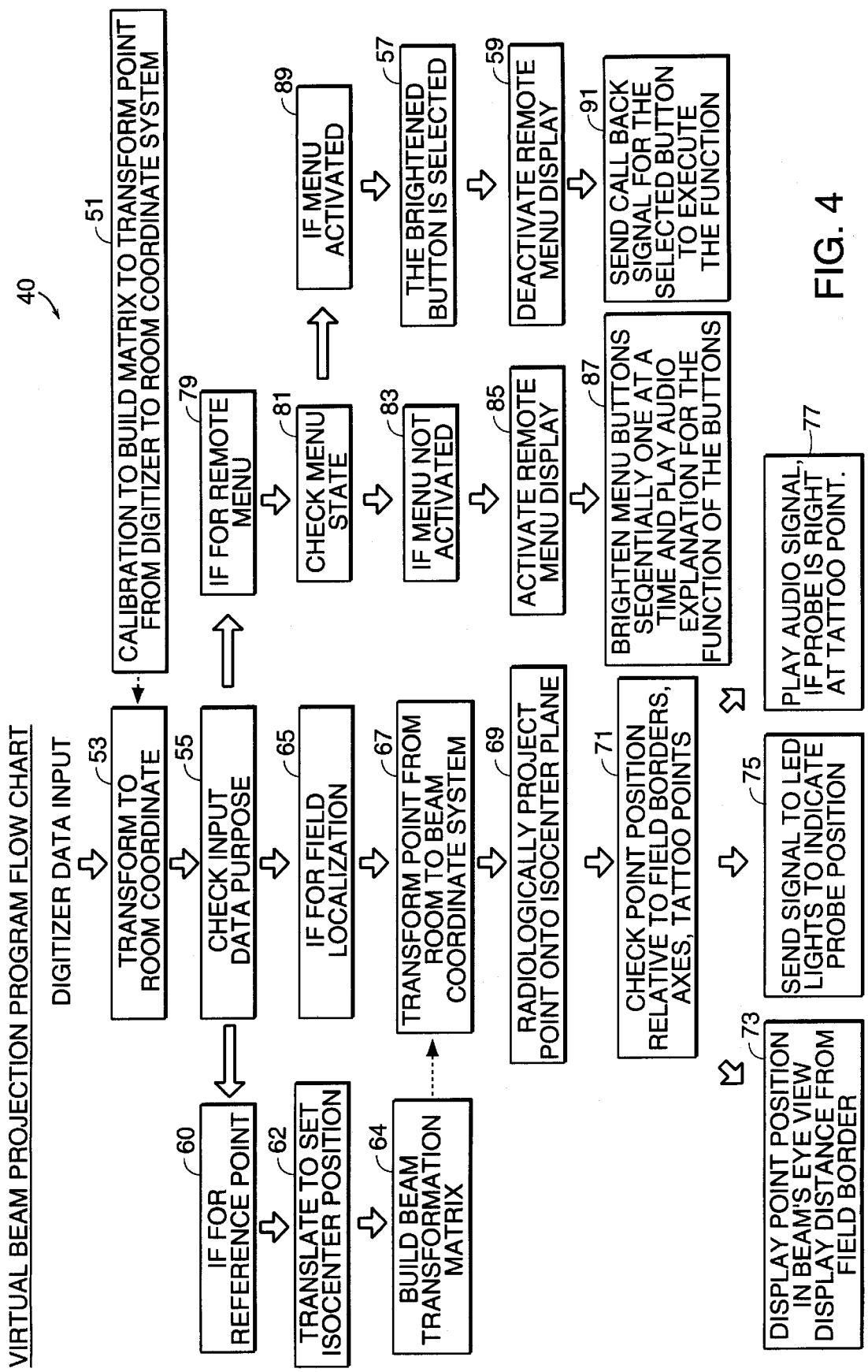
FIG. 4 is a flow diagram of the FIG. 1 embodiment of the present invention.

Referring to FIG. 4, a flow diagram of the computer program 40 of the present invention is illustrated. Initialization of the program 40 begins with initial operation of probe 19 and digitizer 15 during calibration. During calibration, program 40 (at Step 51) builds a matrix to transform a current point digitized by the digitizer assembly 15, 17, 19 to the room coordinate system. After calibration when a point is digitized and the digitizer 15 transmits to digital processor 39 digitizer coordinates of the point, software program 40 (at Step 53) transforms the digitized point data to room coordinates based on the prior calibration. At the next Step 55, the software program 40 determines the purpose of the current input data. If the purpose is to register a reference point (at decision juncture 60), then the software program 40 translates the current digitizer point location to set an isocenter position 62. Next (at Step 64), the software program 40 builds a transformation matrix for transforming room coordinates to radiation beam coordinates. This beam transformation matrix is used later as described below.

If the purpose of the initial input data is for field localization 65, then at Step 67 software program 40 transforms the digitized point data from the room coordinate system to the radiation beam coordinate system. This Step 67 employs the beam transformation matrix previously built at Step 64 during the registration of a reference point (isocenter). Next the software program 40 projects the digitized point onto the isocenter plane at Step 69. Following Step 69, the software program 40 determines the digitized point's position relative to the radiation field borders, axes and tattoo (predefined) points (at Step 71). In turn, the software program 40 displays the digitized point positionally or locationally overlaid on the intersection of the radiation beam with the patient.

That is, at Step 73, program 40 displays on computer monitor 25 a screen view of the location of the digitized point with respect to the radiation beam field (i.e., as seen in the beam's eye view). Program 40 also concurrently displays an indication of the distance of the digitized point (location) from the radiation field border. At the same time, the software program 40 sends a signal 75 to the LED light panel 21, to illuminate a corresponding light pattern, for indicating the digitized point's position with respect to the radiation beam (and hence indicate probe position). Also, the software program 40 generates an audio signal to be sounded if the digitizer probe 19 is pointed to a predefined (e.g., tattoo) point at Step 77.

At Step 79, if the software program 40 determines that the input data is for requesting the remote menu, then software program 40 follows Steps 81, 83, 85, 87, 89, 57, 59 and 91. In particular, the software program 40 checks the menu state 81.

If the menu is not currently activated at 83, then program 40 activates the remote menu (Step 85), such that the remote menu is displayed in the current screen view on computer monitor 25. Program 40 next (i) brightens or illuminates each menu selection sequentially, one at a time, and (ii) generates a audible explanation, played through speakers 27, for the corresponding function of each menu selection. This is illustrated at Step 87.

If the menu is active when program 40 checks the menu status at Step 81, then program 40 considers the currently highlighted button/activation area of the menu, to be selected by the user 57. That is, upon user signal from operating digitizer probe 19 in this mode of operation of program 40, program 40 at Step 57 initializes the task corresponding to the highlighted button. Next program 40, at Step 59, deactivates display of the remote menu on computer monitor 25. At Step 91, program 40 transmits a call back signal to processor 39 to execute the corresponding function/task for the selected menu item.

The foregoing discussion of FIG. 4 illustrates supporting software for one embodiment of the present invention. This discussion is for purposes of illustration and not limitation of the present invention. Other software program configurations and means for implementing the present invention system and apparatus are suitable and within the purview of one skilled in the art.

EQUIVALENTS

While the invention has been particularly shown and described with reference to a preferred embodiment thereof, it will be understood by those skilled in the art that various changes in form and details may be made therein without departing from the spirit and scope of the invention as defined by the appended claims.

For example, during CT-simulation, the invention system digitizes points of clinical or anatomical interest, e.g., breast tissue extent, excisional scar position, to see if they are included in the radiation field with sufficient margin.

The invention system also enables the user to cruise the digitizer probe on the patient to locate the radiation field borders and the specific field points with respect to the patient, for patient marking.

The invention system also uncomplicates planning and patient setup procedures involving the matching of multiple radiation fields, since all the field borders can be digitized and checked for consistency before any radiation is delivered. That is, the invention system may be used in conjunction with the treatment unit to ensure proper setup of the patient.

The invention system may be coupled to a conventional radiation treatment simulation system or other simulation system in addition to CT simulators. That is, the digital processor 39 is coupled to receive radiation beam geometry and other data from the radiation treatment simulator. As such, the invention enables body contour and other information to be captured.

The type of transmitter and detector in the 3D digitizer assembly may be other than the sonic approach as described in the foregoing discussion of the present invention. Also the digitizer probe 19 may be coupled to the digitizing processor member 15 in a cordless fashion using remote control technology and the like.

What is claimed is:

1. Apparatus for correlating a subject area with respect to a radiation beam, the radiation beam having a respective coordinate system, comprising:

a digitizer probe formed of a handle and an elongate body having one end coupled to the handle and a distal end opposite the one end across the length of the elongate body, the distal end for pointing to a point on the subject area, the handle having a transmitter for generating a working signal;

a 3-D digitizer having (i) a receiver spaced apart from the digitizer probe and the subject area for receiving the working signal from the transmitter, and (ii) digitizing means coupled to the receiver and responsive to the received working signals, the digitizing means calculating and digitizing coordinates of the point on the subject area pointed to by the probe distal end in a coordinate system of the 3-D digitizer, such that the 3-D digitizer generates digitizer coordinates of the point;

a computer processor assembly coupled to the 3-D digitizer for receiving the digitizer coordinates of the point and transforming the digitizer coordinates into coordinates of the radiation beam coordinate system; and a display assembly coupled to the computer processor assembly for displaying an indication of location of the point pointed to by the distal end of the probe with respect to intersection of the radiation beam with the subject area, such that the subject area is able to be correlated to the radiation beam.

2. Apparatus as claimed in claim 1 wherein the transmitter generates a sound wave signal for the working signal;

the receiver includes a plurality of microphones for receiving the sound wave signal at different distances and hence different times, the receiver recording the different receipt times; and the digitizing means employs a triangulation calculation for determining distance based on the different receipt times, and from the determined distance, the digitizing means determines digitizer coordinates of the point.

3. Apparatus as claimed in claim 1 wherein the computer processor assembly further supports use of the probe as a computer input device when the point pointed to by the distal end is outside a threshold distance.

4. Apparatus as claimed in claim 1 wherein the computer processor assembly is further coupled to receive radiation beam data from a radiation treatment planning simulation system.

5. Apparatus as claimed in claim 1 wherein the display assembly includes a monitor for displaying a screen view indication of the radiation beam coordinate system overlaid with the indication of the location of the point pointed to by the probe distal end.

6. Apparatus as claimed in claim 5 wherein the display assembly includes an LED light assembly coupled to the probe for indicating location of the point pointed to by the probe distal end relative to boundaries of the radiation beam as intersected with the subject area.

7. Apparatus as claimed in claim 6 wherein the LED light assembly includes a red light for indicating that the point lies outside of the radiation beam boundaries, a yellow light for indicating that the point lies on the radiation beam boundaries and a green light for indicating that the point lies inside the radiation beam boundaries.

8. Apparatus as claimed in claim 7 wherein the LED light assembly further illuminates the green light and yellow light together for indicating that the point lies inside the radiation beam boundaries and on one of an x axis and y axis of the radiation beam.

9. Apparatus as claimed in claim 7 wherein the LED light assembly simultaneously illuminates the red light, yellow light and green light to indicate that the point lies on a predefined field point.

10. A method for aligning a subject area with respect to a radiation beam, the radiation beam having a respective coordinate system, comprising the steps of:

digitizing a point on a subject area, said digitizing generating digitizer coordinates of the point;

transforming the digitizer coordinates of the point into coordinates of the radiation beam coordinate system;

using the radiation beam coordinates of the point, displaying an indication of location of the point with respect to intersection of the radiation beam with the subject area, such that the subject area is able to be correlated to the radiation beam.

11. A method as claimed in claim 10 wherein the step of digitizing includes:

providing a 3-D digitizer assembly including a digitizer probe and a 3-D digitizer, the digitizer probe being formed of a handle and an elongate body having one end coupled to the handle and a distal end opposite the one end across the elongate body, the distal end for pointing to a point on the subject area, the handle having a transmitter for generating a working signal, and the 3-D digitizer having (i) a receiver spaced apart from the digitizer probe and the subject area for receiving working signals from the transmitter, and (ii) digitizing means coupled to the receiver and responsive to received working signals;

using the 3-D digitizer assembly, digitizing the point on the subject area by:
(a) pointing the probe distal end to the point,
(b) enabling the transmitter to generate a working signal in association with the pointing of the probe distal end to the point on the subject area,
(c) receiving the working signal at the receiver, and
(d) responding to the received working signal by the digitizing means calculating coordinates of the point in a coordinate system of the 3-D digitizer, such that the 3-D digitizer generates the digitizer coordinates of the point.

12. A method as claimed in claim 11 wherein the step of the digitizing means calculating coordinates of the point includes the digitizing means employing a triangulation calculation for determining distance between the transmitter and receiver, and from the determined distance, the digitizing means determining digitizer coordinates of the point.

13. A method as claimed in claim 11 wherein the step of transforming the digitizer coordinates of the point includes coupling a computer processor assembly to the 3-D digitizer for receiving the digitizer coordinates of the point and transforming the digitizer coordinates into coordinates of the radiation beam coordinate system; and the step of displaying includes coupling a display assembly to the computer processor assembly for displaying the indication of location of the point pointed to by the distal end of the probe with respect to intersection of the radiation beam with the subject area, such that subject area is able to be aligned with the radiation beam.

14. A method as claimed in claim 13 further comprising the step of the computer processor assembly receiving radiation beam data from a radiation treatment planning simulation system.

15. A method as claimed in claim 13 wherein the step of coupling the display assembly includes providing a monitor for displaying a screen view indication of the radiation beam coordinate system overlaid with the indication of the location of the point pointed to by the probe distal end.

16. A method as claimed in claim 13 wherein the step of coupling the display assembly includes providing an LED light assembly for indicating location of the point pointed to by the probe distal end, relative to boundaries of the radiation beam as intersected with the subject area.

17. A method as claimed in claim 16 wherein the step of providing an LED light assembly includes providing a red light for indicating that the point lies outside of the radiation beam boundaries, a yellow LED for indicating that the point lies on the radiation beam boundaries, and a green LED for indicating that the point lies inside the radiation beam boundaries.

18. A method as claimed in claim 17 further comprising the step of illuminating the green and yellow LED together to indicate that the point lies inside the radiation beam boundaries and on one of an x axis and y axis of the radiation beam field.

19. A method as claimed in claim 17 further comprising the step of simultaneously illuminating the green, yellow and red LED's to indicate that the point lies on a predefined field point of interest.

20. A method as claimed in claim 13 further comprising the step of using the digitizer probe as an input device to the computer processor assembly.

* * * * *